(12) United States Patent
Pal et al.

(10) Patent No.: US 8,038,630 B2
(45) Date of Patent: *Oct. 18, 2011

(54) FLOATING PROBE FOR ULTRASONIC TRANSDUCERS

(75) Inventors: Dharmendra Pal, Miami Lakes, FL (US); Thomas Peterson, Erie, PA (US); Tao Song, Erie, PA (US); Shu Du, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 637 days.

This patent is subject to a terminal disclaimer.

(21) Appl. No.: 11/980,910

(22) Filed: Oct. 30, 2007

(65) Prior Publication Data

US 2008/0061784 A1   Mar. 13, 2008

Related U.S. Application Data

(62) Division of application No. 10/729,628, filed on Dec. 4, 2003, now Pat. No. 7,387,612.

(51) Int. Cl.
*A61H 1/00* (2006.01)

(52) U.S. Cl. .......................................... 601/2; 606/168

(58) Field of Classification Search ................... 600/439, 600/464, 461; 601/2; 604/22; 606/27, 167–169; 451/165; 408/17, 700; 433/86, 119
See application file for complete search history.

(56) References Cited

U.S. PATENT DOCUMENTS

| 3,683,470 | A | * | 8/1972 | McMaster et al. | ............ 29/33 K |
| 4,016,436 | A | * | 4/1977 | Shoh | .............................. 310/322 |
| 6,875,220 | B2 | * | 4/2005 | Du et al. | ........................ 606/169 |
| 7,387,612 | B2 | * | 6/2008 | Pal et al. | ............................ 601/2 |

* cited by examiner

*Primary Examiner* — Parikha Mehta
(74) *Attorney, Agent, or Firm* — Ulmer & Berne, LLP

(57) ABSTRACT

The present invention relates to a device with an ultrasonic-based probe for drilling and coring. The invention uses ultrasonic and subsonic vibrations produced by a frequency compensation coupler or free mass to produce the hammering action of a partially disengaged probe, with a relatively low axial force required. The invention can also be fitted with irrigation and aspiration capabilities. The invention can furthermore be furnished with a body sensor-feedback apparatus, which provides feedback to the operator as to the optimal frequency and power use of the generator. One embodiment of the invention also has a cooling mechanism to keep the drill or coring apparatus at an optimum temperature.

3 Claims, 9 Drawing Sheets

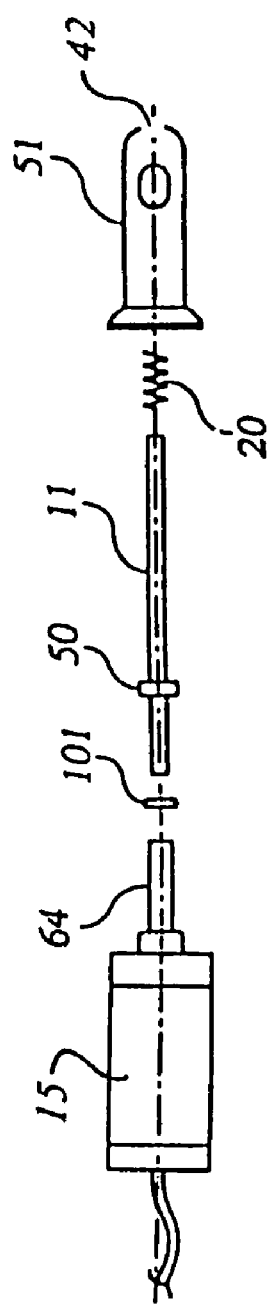
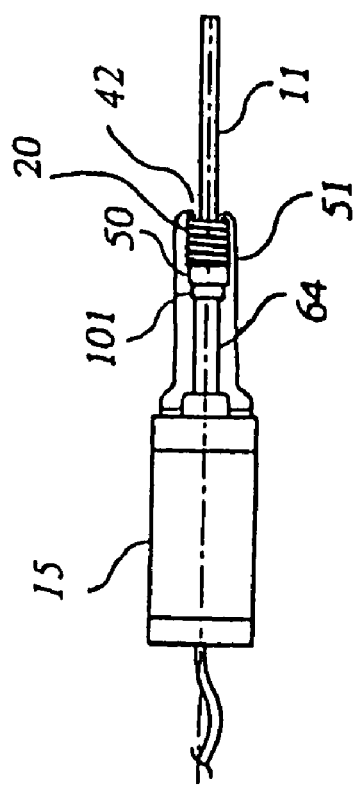
FIG.1a
FIG.1b

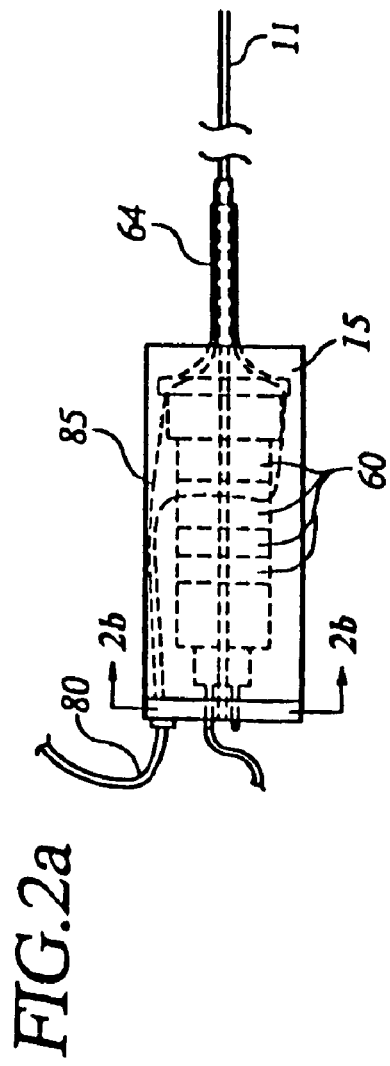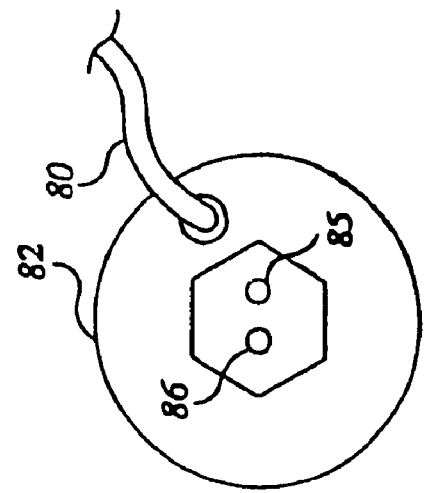
FIG.2a
FIG.2b

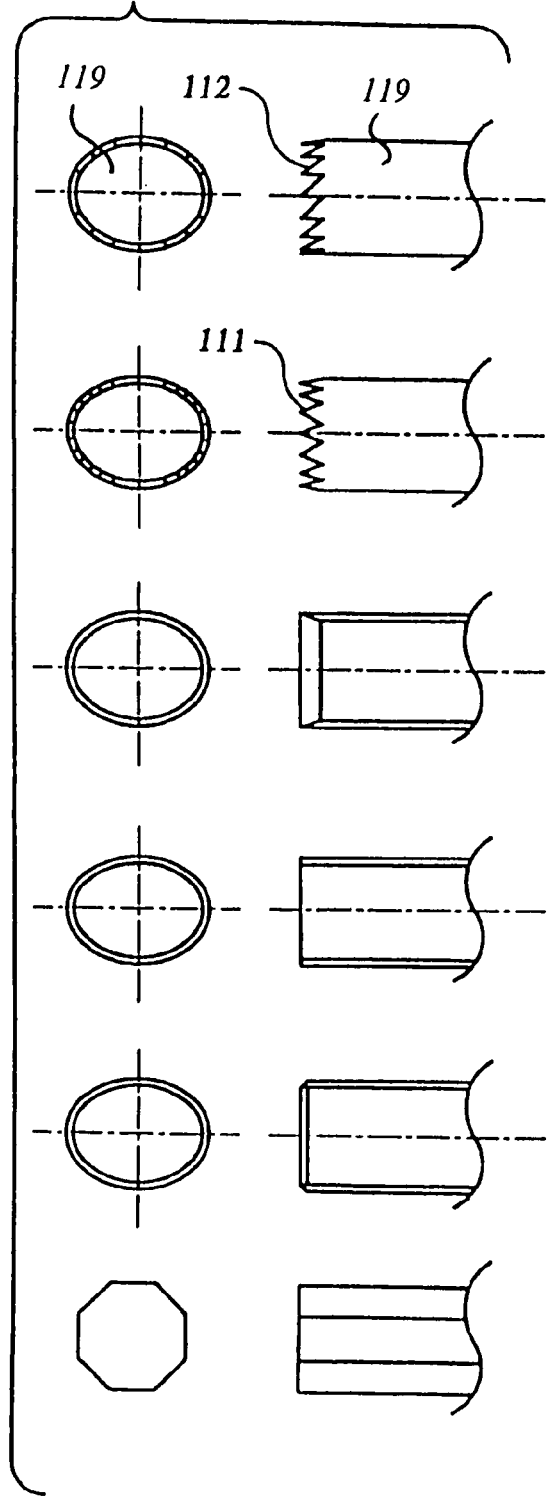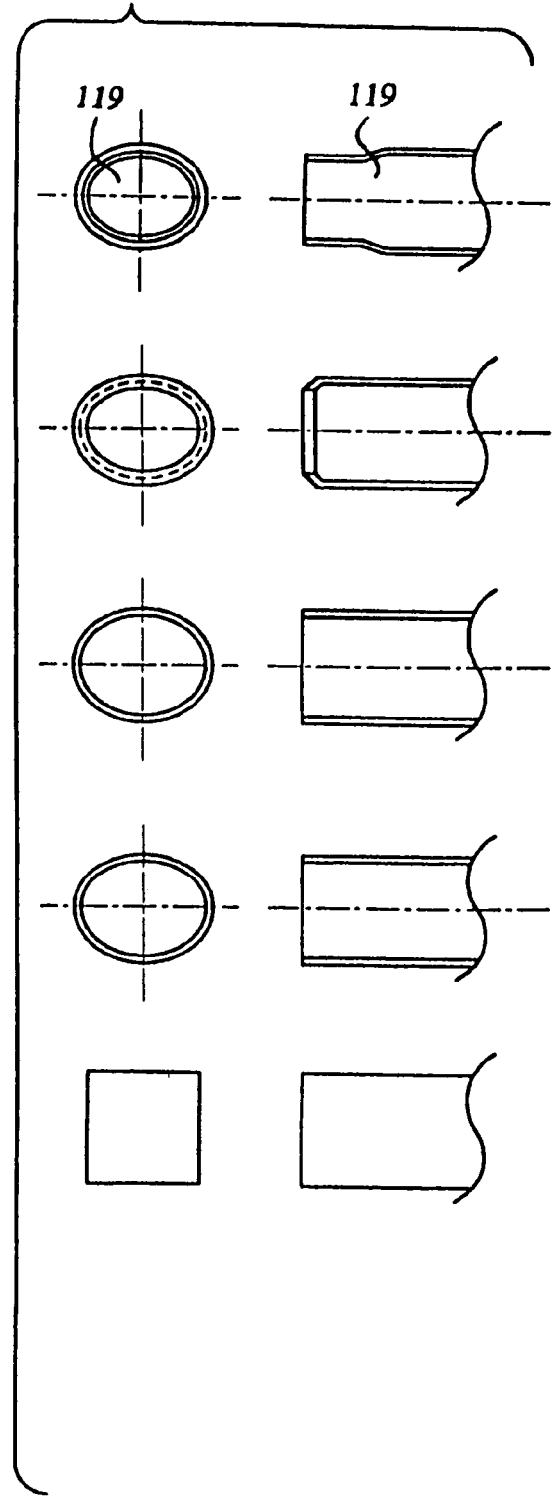

FLOATING PROBE FOR ULTRASONIC TRANSDUCERS

CROSS-REFERENCE TO RELATED APPLICATION

This application is a divisional patent application of U.S. Non-Provisional patent application Ser. No. 10/729,628, filed Dec. 4, 2003, which has issued as U.S. Pat. No. 7,387,612. This application claims priority to U.S. Non-Provisional patent application Ser. No. 10/113,141, filed Mar. 28, 2002, which has issued as U.S. Pat. No. 6,689,087, which claims priority to U.S. Provisional Patent Application Ser. No. 60/279,427 filed Mar. 28, 2001, now abandoned, both of which are incorporated herein in their entireties.

FIELD OF INVENTION

The present invention relates to an ultrasonic drill and corer. More particularly, the invention relates to the combination of ultrasonic and sonic vibrations for drilling with a relatively low axial-force.

BRIEF DESCRIPTION OF THE DRAWINGS

FIG. 1a depicts the components of one embodiment of the invention in an exploded fashion in the order in which the components are fitted together.

FIG. 1b depicts the components of one embodiment of the invention in which the components shown in FIG. 1a are fitted together.

FIG. 2a shows a cross-sectional view of one embodiment of a fixed ultrasonic probe with a cooling mechanism.

FIG. 2b is a view of the fixed ultrasonic probe of FIG. 2a as taken on the line 2b of FIG. 2a.

FIGS. 7a and 7b show a series of tip configurations that can be used on the ultrasonic floating probe.

DETAILED DESCRIPTION OF EMBODIMENTS OF THE INVENTION

Figure 3:
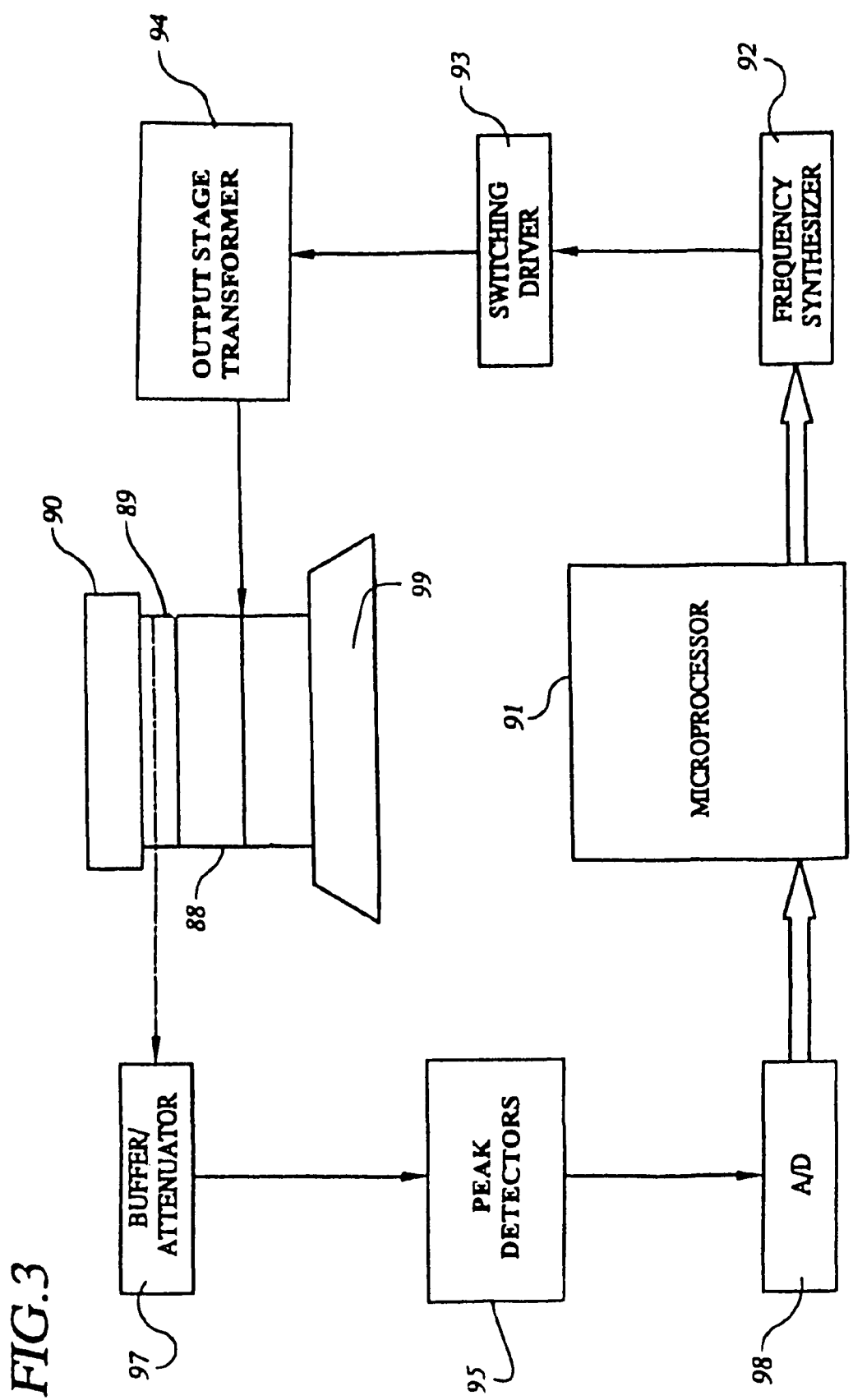
FIG. 3 shows a flowchart for one embodiment of the feedback loop for displacement sensing of the body sensor.

Referring now to the drawings in detail, for ease of the reader, like reference numerals designate identical or corresponding parts throughout the views depicted in the drawings. It should be noted that a drawing does not depict each embodiment of the present invention; nor is each of the notable applications of the present invention depicted by a drawing.

The present invention uses a floating-head drilling mechanism, where high frequency ultrasonic vibrations are induced by a piezoelectric stack actuator electrically connected to an ultrasonic generator and enhanced by an ultrasonic horn. The high frequency ultrasonic vibrations are induced by the piezoelectric stack and are used to create a hammering action with both longitudinal and transverse motion being transferred to the floating head probe. The floating head is a mechanical frequency transformer, and the drill bit operates with a combination of ultrasonic and subsonic frequencies. One example is a transformer which converts 20 kHz ultrasonic drive frequency to a combination of this high frequency drive signal and a 10-10,000 Hz sonic hammering action. These values are not intended to be limiting as many other values can be used, depending on the application. The device presents a low power, misalignment-tolerant device that can include a self-extracting debris process and offers hammering, chiseling, cutting, rotating, and digging capabilities. The device can further be modified to include irrigation and aspiration capabilities.

FIG. 1 shows the components of one embodiment of the invention in an exploded fashion in the order in which the components are fitted together, and FIG. 1b shows the same components after being fitted together. In the embodiment shown in FIGS. 1a and 1b, the ultrasonic frequencies are generated by piezoelectric ceramics or crystals (not shown) contained within housing 15. As used herein, "piezoelectric ceramics" will be used to refer to piezoelectric ceramics, piezoelectric crystals, and piezoceramics. The high frequency vibrations generated by the ultrasonic generator (not shown) are enhanced by ultrasonic horn 64 which amplifies the ultrasonic vibrations that are induced by the ultrasonic generator. Resonator probe (or drill bit, floating-head probe, or drilling mechanism), hereinafter probe 11, is inserted into horn 64, which, in turn, is driven by the generator. Probe 11 is not, however, fixedly secured to horn 64, but allowed to partially disengage horn 64 by using a capturing mechanism. One embodiment of the capturing mechanism is comprised of barrier member 50 and capturing member 51.

When assembled, as shown in the embodiment of FIG. 1b, capturing member 51 covers horn 64 and includes opening 42 in capturing member 51 large enough for the tip of probe 11 to fit through. Probe 11 also has barrier member 50 that is fitted on probe 11. Thus, probe 11 is actually a "floating probe" because probe 11 partially disengages horn 64 during the ultrasonic frequency cycles. However, one of ordinary skill in the art will recognize that other capturing mechanisms could be used to perform the same function.

Figure 5A:
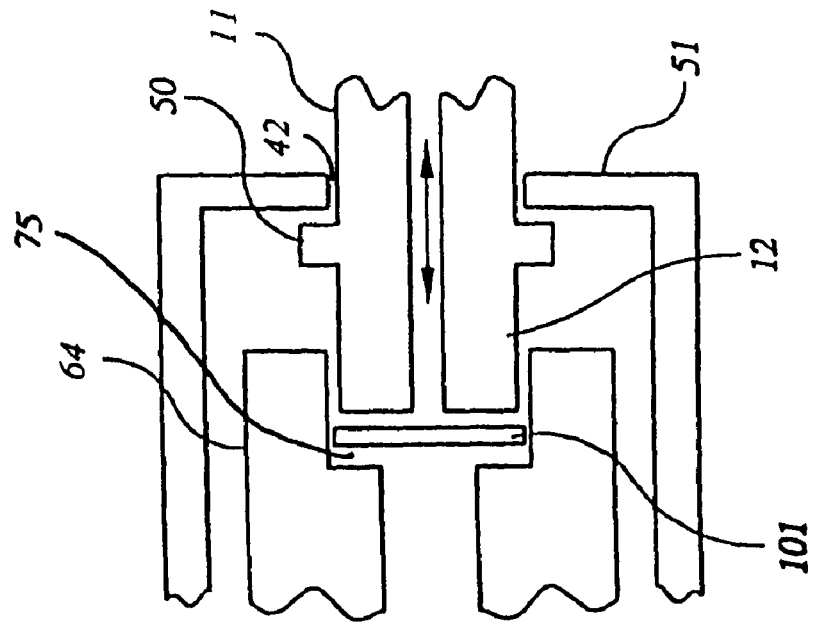
FIGS. 5a and 5b each show a cross-sectional view of two possible positions of the free mass of the ultrasonic floating probe.
Figure 5B:
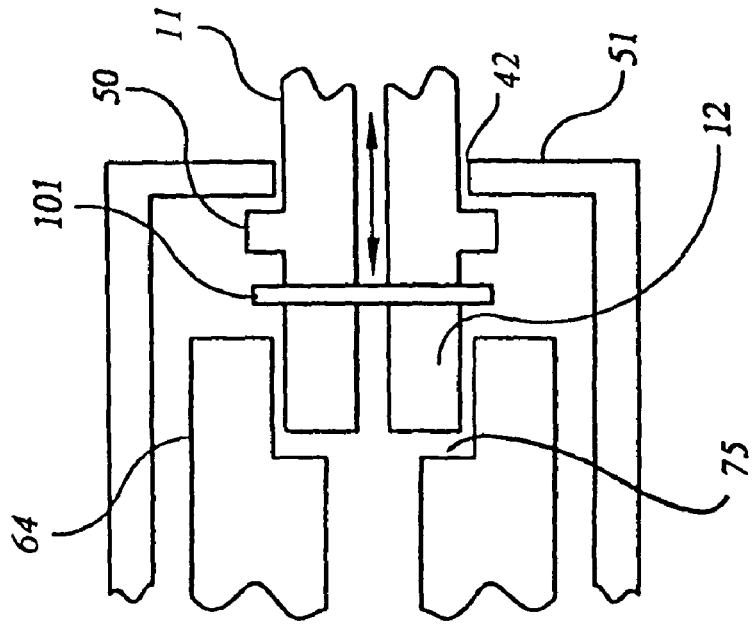

In the embodiment shown, barrier member 50 is closer to the end of probe 11 that is to be inserted into horn 64 than it is to the end that protrudes from capturing member 51 when assembled, but could be at any point along probe 11. Barrier member 50 is larger than opening 42 to prevent probe 11 from disengaging horn 64 completely. Barrier member 50 can be fixedly secured on probe 11 between horn 64 and capturing member 51 or probe can barrier member 50 can be constructed as one integrated piece as can be seen in FIGS. 5a and 5b. In addition, spring 20 can be included as part of the capturing mechanism and is shown in the embodiment of the present invention depicted in FIGS. 1a and 1b. Spring 20 is located between barrier member 50 and capturing member 51 and provides extra force in pushing probe 11 back into horn 64 after probe 11 disengages horn 64. In one embodiment, spring 20 is compressed to one eighth of an inch (⅛"). This compression allows probe 11 to work without being under load, i.e., the device can be operated without a user having to exert a downward force against an object. In addition to spring 20, a bell-view washer or cantilever-type spring or spring-like material can be used, as can any other load mechanism known to one of ordinary skill in the art. With respect to the amount of bias in spring 20, the eighth of an inch is a little more than the length of excursion of the end of probe 11, as it travels back and forth.

Capturing member 51 can be constructed in a variety of geometric shapes, two of which are shown in the drawings of this application. However, one of ordinary skill in the art will readily appreciate that capturing member 51 may be constructed in alternate geometric shapes so long as capturing member 51 has opening 42 to allow probe 11 to fit through and provides a surface to stop probe 11 from completely disengaging horn 64.

FIG. 1 also depicts the frequency compensation coupler or free mass 101 that is used with this embodiment of the present invention to enhance the conversion of the ultrasonic frequencies to subsonic frequencies. Free mass 101 is a metal disk or washer that slides on and engages probe 11. As used herein, the term "free mass" is defined as any piece of material (metal or otherwise) that is not fixedly attached to any other component, and is used to enhance the jack-hammering effect of the device for certain applications. Free mass 101 is made of almost any strong material since it may be the weakest component of the ultrasonic probe assembly. Examples of materials that may be used are steel (including stainless steel), titanium, or other similar metals, or alloys of these metals. However, one of ordinary skill in the art will readily appreciate that other materials may be used with the device.

Free mass 101 is located between barrier member 50 of probe 11 and the end of probe 11 that is inserted into horn 64. Free mass 101 oscillates between horn 64 and barrier member 50 of probe 11 and reduces probe frequency from a higher frequency to a lower frequency. Free mass 101 acts as a modulator between the low frequency of the probe and the high frequency of the transducer unit. Thus, free mass 101 converts ultrasonic action into subsonic action. This is desirable in some applications because the subsonic action creates less heat and performs better than at ultrasonic frequencies.

In operation, as the piezoelectric ceramics rapidly expand and contract, contact horn 64, which in turn hits free mass 101, which then hits probe 11, urging it forward. Probe 11 is then urged back against horn 64, either by spring 20 or some other load mechanism, or by the user exerting a downward force on the device. Free mass 101 contacts probe 11 whether on its end surface (as can be seen in the embodiment of FIG. 5*b*) or contacts barrier member 50 on probe 11 (as can be seen in the embodiment shown in FIG. 5*a*). This is repeated many times per second, producing the jack hammer-like effect of the device.

One of ordinary skill in the art should also appreciate that in addition to the materials used, free mass 101 can vary in size, shape, and weight. Exactly what size, shape, and weight chosen depends on the size of transducer horn 64, probe 11, and on the frequency output at which the device is to be operated. The diameter of free mass 101 should be at least as great as that of the tip of horn 64 to prevent probe 11 from being ejected through opening 42 of capturing member 51, but small enough not to scrape the side walls of capturing member 51. For applications such as drilling hardened materials, as described herein, free mass 101 is, in one embodiment, one quarter (¼) inch in diameter. For applications such as the removal of pacemaker leads, free mass 101 can also be one quarter inch in diameter. However, the inner diameter and outer diameter of probe 11 is dependent on the diameter of the hole size required or the diameter of the item going through the inside of probe 11 such as a pacemaker lead to be removed. Thus, the size of free mass 101, in this particular application, is also a function of the lead to be removed. In another example embodiment, free mass 101 is 5 cm (five centimeters) in diameter when used for drilling and coring ice at −30° C.

Figure 6A:
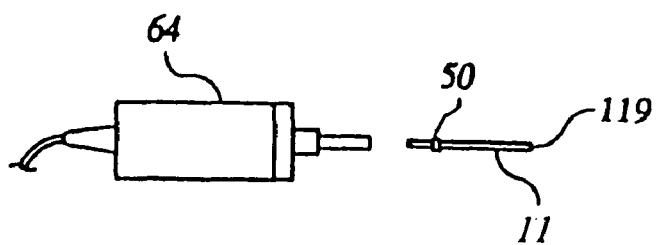
FIGS. 6a, 6b, 6c, and 6d show four possible assemblies of the ultrasonic floating probe.
Figure 6B:
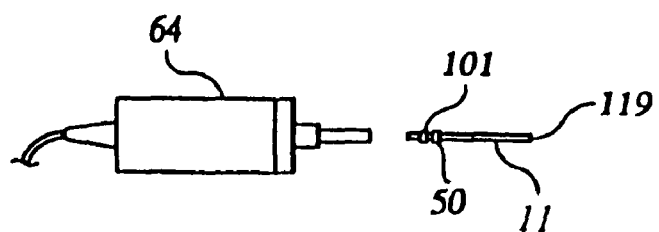
Figure 6C:
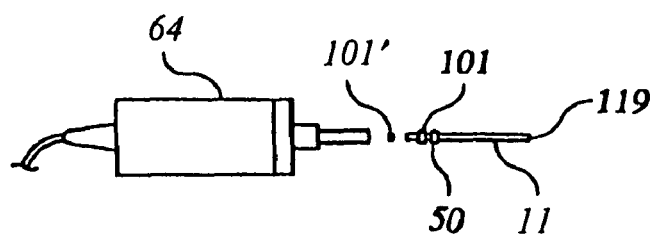

It should also be appreciated that more than one free mass 101 could be employed, as can be seen in FIG. 6*c* for example. Free mass 101 allows the use of probes 11 of different lengths with the same frequency transducer. As is known in the art, varying the length of probe 11 would normally require modifying the transducer's frequency. The use of free mass 101 eliminates the need to tune the transducer to the different probe 11 lengths.

FIG. 2*a* shows one embodiment of a cooling mechanism for cooling the fixed ultrasonic probe for those uses that may require cooling the device, e.g. some biological applications, and FIG. 2*b* is a view of the ultrasonic floating probe as taken on the line 2*b* of FIG. 2*a*. In FIGS. 2*a* and 2*b*, piezoelectric ceramics 60, which generate the ultrasonic frequencies that emanate to horn 64, electrical connection 80, inlet port 85, exit port 86, and bolt 82 can all be seen.

In FIG. 2*b*, bolt 82 can be seen, which is used to compress piezoelectric ceramics 60. Within bolt 82 is inlet port 85 and outlet port 86, running essentially the length of bolt 82. A saline solution is pumped through bolt 82 via inlet port 86, passes through and cools horn 64, and then exits bolt 82 via exit port 86. In one embodiment of this cooling mechanism, the saline coolant is pressurized to force it into bolt 82 and is attached to a vacuum to draw it out.

It should be clear to one of ordinary skill in the art that the cooling mechanism shown and described in FIGS. 2*a* and 2*b* may be necessary only for heat-sensitive applications such as some biomedical applications. The combination of floating probe 11 with free mass 101 reduces friction and heat such that for some applications, the use of a cooling system will be unnecessary. Furthermore, it should be obvious to one of ordinary skill in the art that any mechanism for cooling the device, for those applications requiring such, may be employed.

FIG. 3 shows a flowchart of one embodiment for the feedback loop for displacement sensing of the body sensor feedback apparatus. The feedback loop provides the operator with the optimal frequency and power use of the generator. To enable the feedback, transducer 60 is comprised of at least two sensing piezoelectric ceramics 89, which are relatively thin and act as a body sensor, are placed near relatively thick driving piezoelectric ceramics 88, or driving ceramics, and are sandwiched between back mass 90 and front driver 99. When driving piezoelectric ceramics 88 are energized, they exert a force on sensing piezoelectric ceramics 89. This force is translated to an electrical signal by body sensor 89 and sent to microprocessor 91. Buffer/attenuator 97 reduces the voltage level of the body sensor output to a level which control electronics can accept. Peak detector 95 includes rectification and filter, the output of which is proportional to the peak value of the body sensor output. A/D source 98 is an analog to digital converter. Microprocessor 91 then calculates the resonant frequency. The required change in frequency is done by frequency synthesizer 92 which generates the frequency signal. Switching driver 93 is a switch component that generates high power square waveform which has the same frequency of output as frequency synthesizer 92. Output stage driver transformer 94 then boosts the voltage of the electrical signal up to the level that can activate driving piezoelectric ceramics 88. Output stage driver 94 may or may not have impedance matching components. This device provides an instantaneous reading as to the optimal settings under which the transducer assembly should operate. This allows the transducer assembly to stay in tune throughout the use of the transducer.

However, this body sensor-feedback apparatus is only one embodiment, and one of ordinary skill in the art will recognize that components could be combined or changed with other components known to those in the art.

Figure 4B:
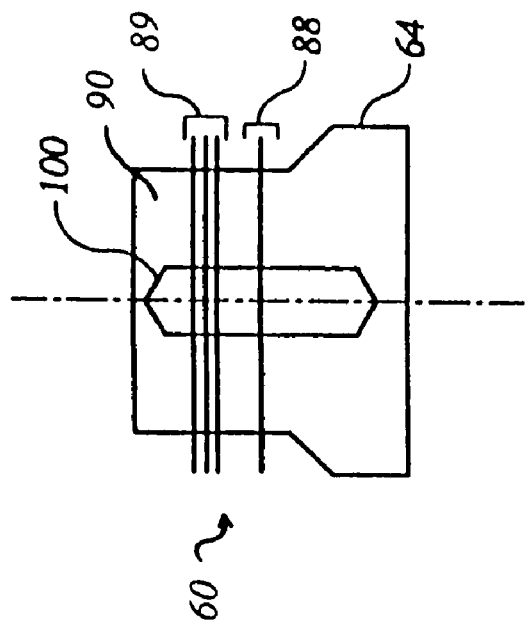
FIGS. 4a and 4b show cross-sectional views of a section of one embodiment of the ultrasonic floating probe that illustrates the piezoelectric sensing crystals.
Figure 4A:
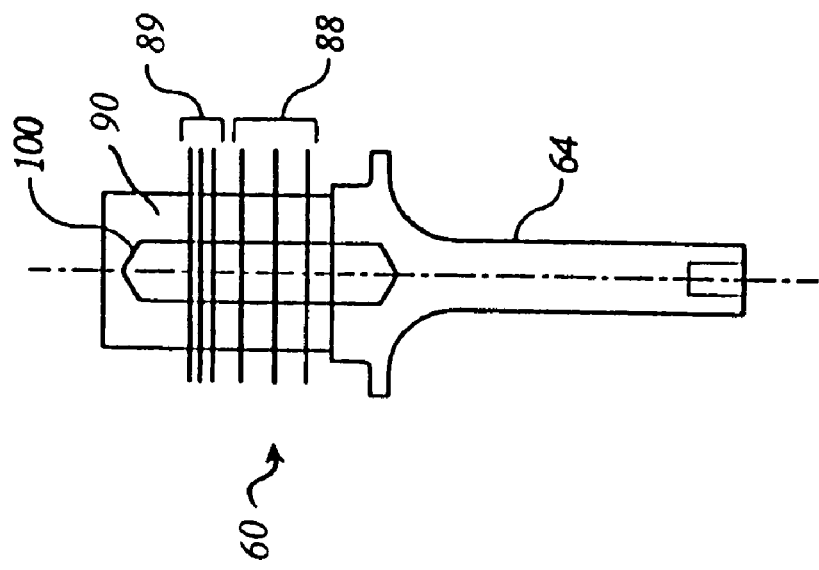

FIGS. 4a and 4b show two cross-sectional views of a section of the ultrasonic floating probe that illustrates sensing piezoelectric ceramics 89 in connection with the body sensor feedback apparatus described and shown in FIG. 3. FIGS. 4a and 4b illustrate the location and connection between driving piezoelectric ceramics 88, which produce the ultrasonic frequencies, and sensing piezoelectric ceramics 89, which provide the feedback to the microprocessor (not shown), in the context of an ultrasonic device as contemplated by the present invention. Sensing piezoelectric ceramics 89 are very thin as compared to driving piezoelectric ceramics 88. The encased stress bolt or biasbolt 100 and horn 64 can also be appreciated in FIGS. 4a and 4b. The stepped shape of horn 64, as seen in FIG. 4b, offers the greatest displacement magnification when compared to other geometries of horns (for example, that of FIG. 4a).

In one embodiment of the invention, the ultrasonic transducer assembly operates as a quarter wave transformer with back mass 90 acting as a mechanical open-circuit, i.e., air-backed. Under this condition, the transducer radiates most of its output energy towards probe 11 and the object to be drilled or cored. In this embodiment, biasbolt 100 contains the transducer assembly and is used to mount the transducer assembly and maintain the strength of piezoelectric ceramics 60 in the stack. When the transducer vibrates under high drive voltages, the tensile stress reaches levels that can fracture piezoelectric material. Biasbolt 100 is tightened to induce compression at a level that slightly exceeds the expected maximum level of tensile stress. To produce a driller/corer head with a hollow center (e.g., when a coolant path is desired or a sensor is employed), biasbolt 100 can be replaced with a threaded tube, located either at the center of the piezoelectric ceramics 60 stack or external to the stack, encircling the sandwiched piezoelectric ceramics 60. In this embodiment, the transducer's induced displacement amplitude is magnified mechanically by front stepped horn 64, which consists of two or more concentric cylinders of different diameters.

FIGS. 5a and 5b provide two embodiments of part of one capturing mechanism for permitting probe 11 to partially disengage horn 64. FIG. 5a shows a cross-sectional view of the section of the ultrasonic floating probe that engages horn 64. In this close-up view of the proximal end of ultrasonic probe 11, the tip of transducer horn 64 can be observed, and the position of free mass 101, relative to the tip of horn 64, can also be seen. As shown in FIG. 5a, free mass 101 fits over probe 11 and is located between barrier member 50 of probe 11 and proximal end 12 of probe 11 that fits into horn 64. Free mass 101 can also be located within annular portion 75 of horn 64, between proximal end 12 of probe 11 and horn 64 as shown in FIG. 5b. In the embodiments shown by FIGS. 5a and 5b, capturing member 51 can also be appreciated. Opening 42 of capturing member 51 is of a smaller diameter than barrier member 50 and prevents probe 11 from fully disengaging horn 64. One of ordinary skill in the art will note that other arrangements between probe 11, barrier member 50, free mass 101, and horn 64 can be envisioned and are contemplated by the present invention. In addition, more than one free mass 101 can be used.

FIGS. 6a through 6f show different assemblies of the ultrasonic floating probe device. In FIG. 6a, a hand-held assembly with a one-piece annular plastic probe 11 inserted into horn 64 is shown, along with barrier member 50. It is possible to have a hand-held assembly due to the relatively low axial pre-load required and because the device is insensitive to alignment. This results in the device being able to be used for angled drilling and coring and is especially useful in low gravity environments.

Figure 6D:
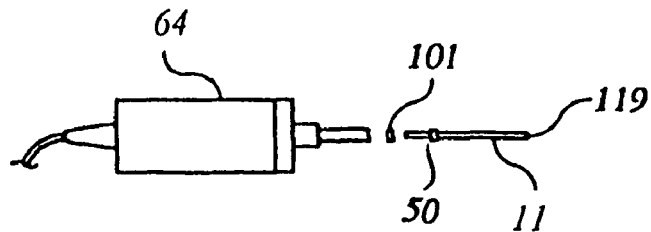

The device produces both longitudinal and transverse motion of probe 11. As a result of these motions, coring bit 119 creates a hole slightly larger in diameter than that of bit 119, reducing the chance of drill bit 119 jamming during drilling and coring. Bit 119 need not be sharp, and various shaped bits 119 can be designed to take advantage of this (see FIGS. 7a and 7b). FIG. 6b illustrates the same assembly as shown in FIG. 6a except that it also shows free mass 101 as assembled in FIG. 5a, i.e., with free mass 101 located on probe 11 between horn 64 and barrier member 50. FIG. 6c shows the same hand-held assembly as shown in FIG. 6b, but with the addition of second free mass 101' located between probe 11 and horn 64. FIG. 6d shows the same hand-held device as shown in FIG. 6a, but with free mass 101 located between proximal end 12 of probe 11 and horn 64 as provided and described in FIG. 5b. If the hammering effect is to be enhanced without affecting the ultrasonic frequency, free mass 101 should be added to the assembly.

Figure 6E:
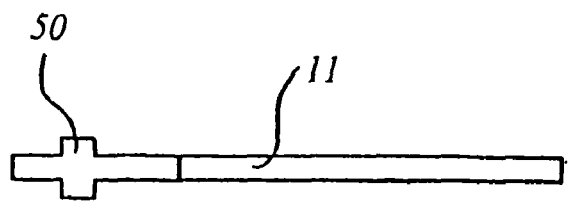
FIG. 6e depicts one embodiment of a multi-piece probe.
Figure 6F:
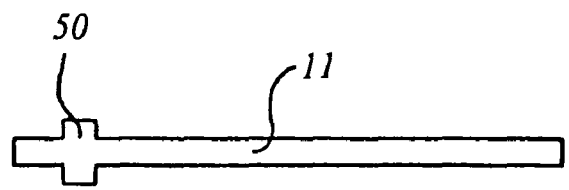
FIG. 6f depicts one embodiment of a one-piece probe.

Furthermore, FIG. 6e depicts a two-piece or multi-piece probe, while FIG. 6f depicts a one-piece probe. It should be noted that in the two-piece construction, the pieces can be made of the same materials or can be made of various materials such as steel and steel alloys (including stainless steel), titanium and titanium alloys, plastic, or other suitable hardened materials. It should be noted that this list is not exhaustive and one of ordinary skill will recognize that other materials could be used. It should also be noted that the one-piece construction, as shown in FIG. 6f, could be made of any of the same materials.

FIGS. 7A and 7B show a series of tip configurations that can be used on the ultrasonic floating probe according to the application. Bits 119 can be constructed as closely-spaced, small diameter rods to allow only the selected sections of the material upon which work is being done to be chipped, or bits 119 can be smooth for slicing applications. Since bit 119 and the probe (not shown) do not rotate, drilling sensors can be integrated near bit 119 to examine and analyze the cored material without the risk of mechanical damage. One or a plurality of sensors of sensor suites can be used to examine the freshly produced surfaces, while penetrating the medium. Furthermore, the sensors can be installed in the core area to examine the cored material where emitted volatiles are sucked by a vacuum system to an analyzer (see also FIG. 8). Potential sensors include temperature, eddy-current, acoustic sensors, dielectrics, fiber optics, and others. Two specific configurations, 111 and 112, are shown which have a fingered construction for coring. The fingered configuration is particularly well-suited for coring bones, one of the possible uses of this device. It will be obvious to one of ordinary skill in the art that any type of bit 119 configuration can be used with the present invention, depending on the application, such as, but not limited to the remaining bit 119 configurations of FIGS. 7a and 7b.

Figure 8:
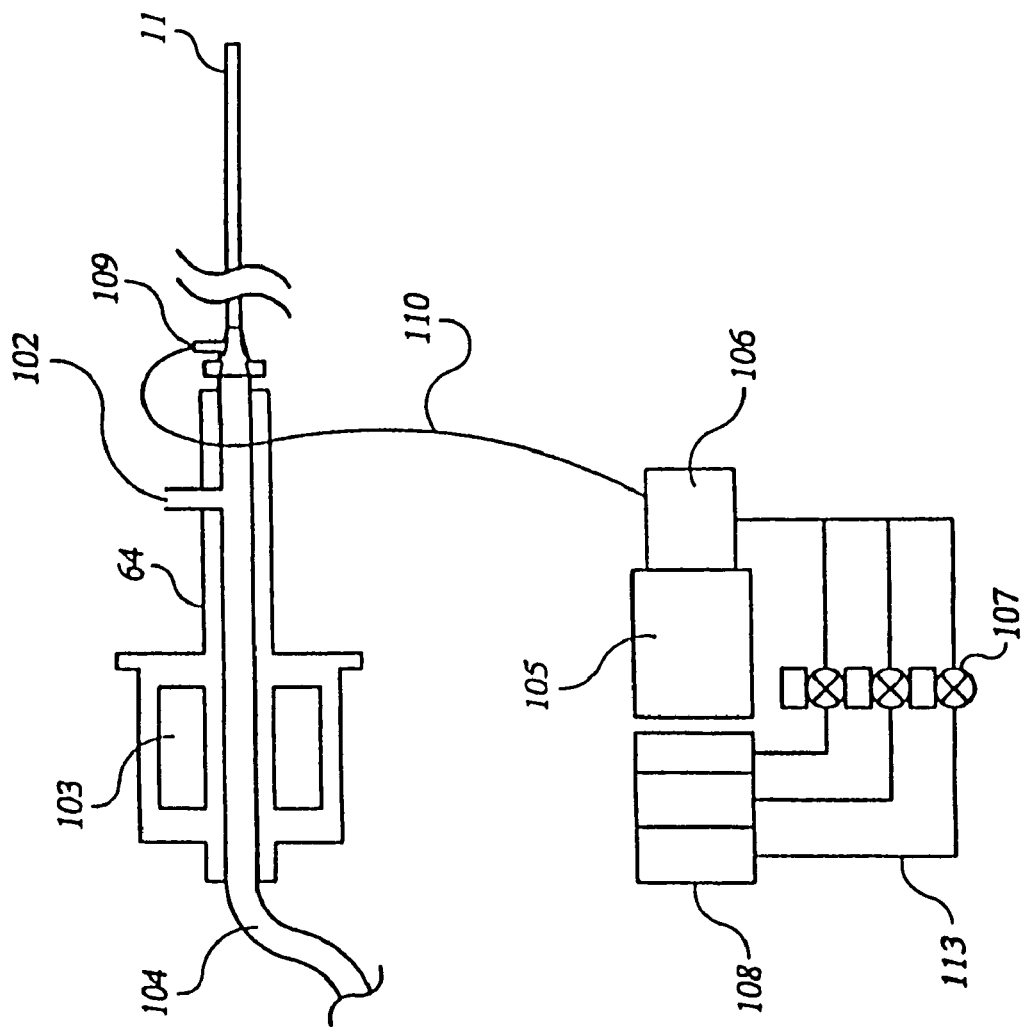
FIG. 8 shows a cross-sectional view of one embodiment of the ultrasonic floating probe with irrigation and aspiration capabilities.

FIG. 8 shows a cross-sectional view of one embodiment of the ultrasonic floating probe with an irrigation and aspiration mechanism. The figure illustrates one example of a free-floating annular probe 11 with an irrigation and aspiration capability in which probe 11 is a corer. At the proximal end of probe 11 is adapter 109 for irrigation. Adapter 109 has irrigation conduit 110, which is connected to pump head 106. Pump head 106 is part of pump 105, which pumps irrigation fluid into probe 11. The pump assembly has a number of tanks 108 which can contain irrigation fluids such as saline. Each tank 108 is connected to the pump head 106 via one or more pump conduits 113 in which the irrigation fluid is pumped through pump conduit 113 by pumps or solenoids 107, for example. In this embodiment, there are two vacuum exits; first vacuum exit 104 for samples and second vacuum exit 102 for dust and volatiles. First vacuum exit 104 and second vacuum exit 102 comprise an aspiration unit. In the embodiment shown, second vacuum exit 102 is located within horn 64 and first vacuum exit 104 is located at the back of the assembly, behind piezoelectric stack 103. One of ordinary skill in the art should appreciate that other configurations in which the various parts of the aspiration unit are located elsewhere on the device.

Figure 9:
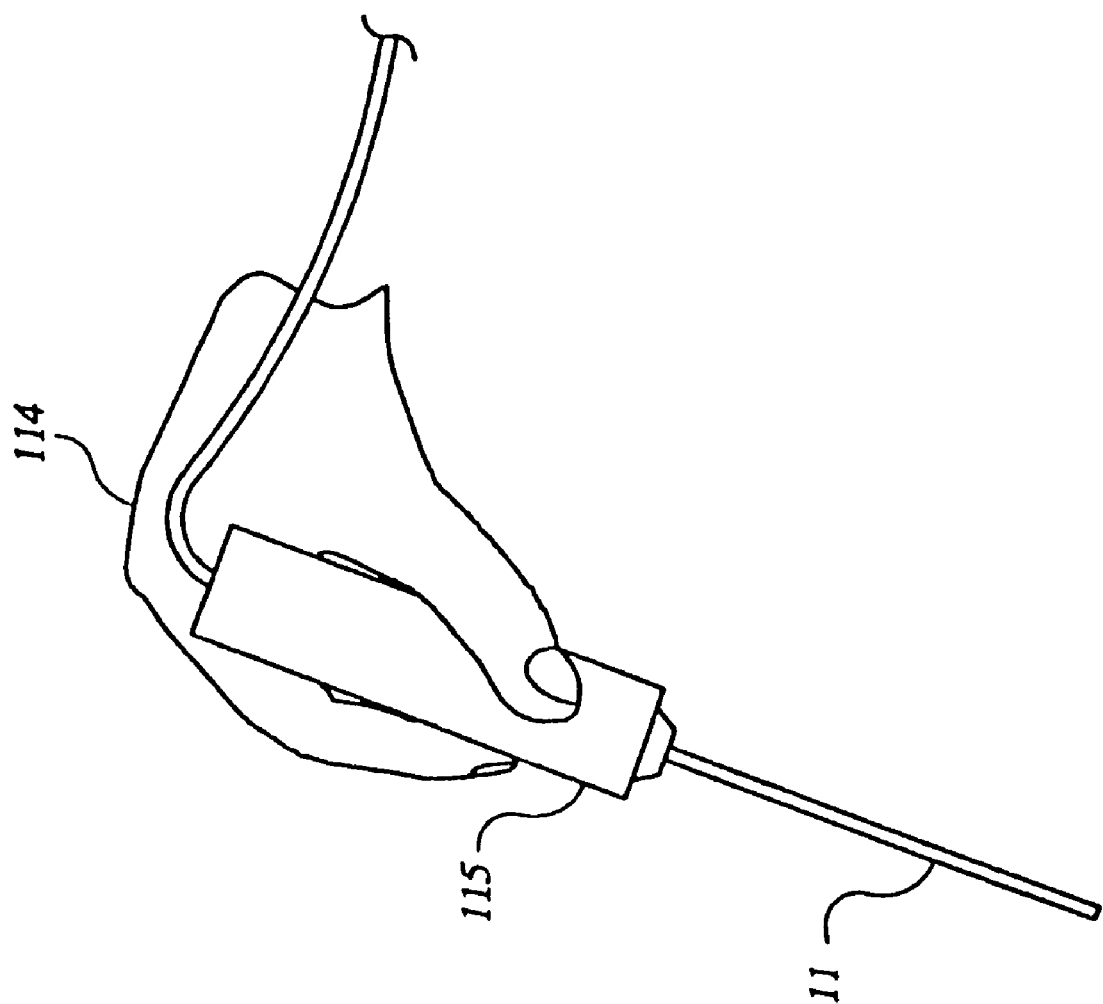
FIG. 9 illustrates the ease of use of one embodiment of the ultrasonic floating probe.

FIG. 9 illustrates the ease of use of the ultrasonic floating probe during use. FIG. 9 shows user's hand 114 and is intended to demonstrate the ease of holding the invention due to the low axial force required to produce the hammering or drilling action. The closed and lightweight handle 115, with the elements (piezoelectric stack, horn, etc.) enclosed within, can be appreciated as well as probe 11. It should be apparent to one of ordinary skill in the art that probe 11 can be of different lengths depending upon the application.

This invention, in any of the embodiments described above, can be used in many applications. A notable application of the subject invention is for bone grafts. The preparation of an autogenous bone graft, allografts, or other substitutes such as corralline hydroxyapatite are all useful applications of the present invention. One of the steps in bone graft is the extraction of the material to be grafted. The use of the present invention, with its coring and sample extraction mechanisms, is especially adapted for this purpose. Another bone graft technique is the use of demineralized bone. Demineralized bone is a cortical allograft bone wherein the removal of surface lipids and dehydration of the bone has been accomplished by diverse solutions such as ethanol or hydrochloric acid. The demineralization removes acid soluble proteins and leaves behind acid-insoluble proteins, bone growth factors, and collagen. The bone treated in this manner can be implanted in strips or processed into smaller particles. It has also been suggested that if holes are drilled into cortical allograft, it can increase the porosity of the bone by allowing a more efficient demineralization. This can result in a bone graft that it is more osteoconductive and osteoinductive. Another use for orthopedic drilling is on hip replacement where a hole must be drilled in the hip that is going to be replaced in preparation for the replacement. Bone marrow samples can also be obtained out of a person's healthy bone for typing or transplant in a less painful way that other procedures presented on the art. Another orthopedic use is for the drilling/coring for the subsequent insertion of pins or screws after an accident or disease to put together and repair the bone of a patient or remove the bone cement in the case of an implant replacement procedure.

The device assembly can also be used to drill through different materials, including but not limited to, basalt, corsite, chalk, and ice. Uses in mining operations and sample-taking on interplanetary explorations are notable applications of the present invention.

Yet another potential use of the device is as a sounding mechanism. The hammering action provides a sounding mechanism for non-invasive probing of the ground geology to provide information about its subsurface structure and mechanical properties. To take advantage of this possibility, accelerometers can be used to sense the elastic waves that are imparted into the ground and analyze the received wave characteristics, providing information about, for example, soil mechanical properties, geological anisotropy, and layered characteristics, as well as detect, locate, and characterize geological cavities, useful in such areas as construction and geological excavation. The method involves transmitting elastic waves through a medium and analyzing the wave energy after interacting with the various geophysical features, layer characteristics, and material and ground physical properties and flaws. As can be seen from Table 1, the elastic moduli of soils and rocks have distinctive ranges that vary in orders of magnitude:

TABLE 1

Typical values of the elastic modulus for soils and rocks

| Soil or rock type and condition | Modulus of Elasticity, E in lb/ft$^2$ | Modulus of Elasticity, E in Pa |
|---|---|---|
| Soft clay | 5K-30K | 0.25K-1.5K |
| Wet soft clay | 30K-200K | 1.5K-10K |
| Medium Clay | 10K-70K | 05K-3.5K |
| Wet medium soil | 100K-100K | 5K-50K |
| Stiff clay | 25K-400K | 1.2L-20K |
| Wet stiff clay | 300K-1,500K | 15K-75K |
| Loose sand | 200K-500K | 10K-25K |
| Medium dense sand | 400K-1,200K | 20K-60K |
| Dense sand | 1,000K-2,000K | 50K-100K |
| Sandstone | $1.4 \times 10^8$-$4c10^8$ | 7M-20M |
| Granite | $5 \times 10^8$-$10 \times 10^8$ | 25M-50M |
| Steel | $4.2 \times 10^9$ | 200M |

Although, for convenience, the method of use and corresponding apparatus of the present invention have been described hereinabove primarily with respect to specific embodiments, it will be apparent to those skilled in the art that many variations of this invention can be made without departing from the spirit of the invention as claimed. The descriptions presented in those embodiments are not intended to demonstrate all of the possible arrangements and modifications to the design. For those skilled in the art, changes will be apparent that will fall within the spirit and the scope of the present invention.

What is claimed is:

1. A method comprising the steps of:
   providing an ultrasonic device comprising;
      a resonator probe, said resonator probe having a proximal end and a distal end;
      a housing;
      a horn fixedly secured to said housing and adapted to receive said proximal end of said resonator probe;
      a plurality of piezoelectric ceramics contained within said housing;
      a capturing mechanism, wherein said capturing mechanism permits said resonator probe to partially disengage said horn;
      a free mass non-fixedly engaging said resonator probe;
      wherein said horn is further comprised of an annular portion, said free mass being positioned within said annular portion of said horn, between said proximal end of said resonator probe and said horn; and
   drilling in human tissue.

2. A method comprising:
   providing an ultrasonic device comprising;
      a resonator probe, said resonator probe having a proximal end and a distal end;
      a housing;
      a horn fixedly secured to said housing and adapted to receive said proximal end of said resonator probe;
      a plurality of piezoelectric ceramics contained within said housing;

a capturing member functionally engaging said horn and at least partially enclosing said resonator probe, wherein said capturing member is comprised of an opening through which said distal end of said resonator probe protrudes and permits said resonator probe to partially disengage said horn;

a barrier member disposed on said resonator probe between said horn and said capturing member and having a diameter larger than said opening of said capturing member;

a free mass functionally engaging said resonator probe;

wherein said horn further includes an annular portion, said free mass being positioned within said annular portion of said horn, between said proximal end of said resonator probe and said horn; and drilling in human tissue.

3. A method comprising:

providing an ultrasonic device comprising;

a resonator probe, said probe having a proximal end and a distal end;

a housing;

a plurality of piezoelectric ceramics contained within said housing;

a horn fixedly secured to said housing and adapted to receive said proximal end of said resonator probe;

a capturing mechanism, wherein said capturing mechanism permits said resonator probe to partially disengage said horn;

a free mass functionally engaging said resonator probe;

an ultrasonic generator for generating ultrasonic vibrations in said plurality of piezoelectric ceramics, wherein said ultrasonic generator is electrically connected to said plurality of piezoelectric ceramics;

wherein said horn is further comprised of an annular portion, said free mass being positioned within said annular portion of said horn, between said proximal end of said resonator probe and said horn; and drilling in human tissue.

* * * * *